United States Patent
Brown

[11] Patent Number: 6,032,065
[45] Date of Patent: *Feb. 29, 2000

[54] SENSOR MASK AND METHOD OF MAKING SAME

[75] Inventor: Charles E. Brown, Leavenworth, Kans.

[73] Assignee: Nellcor Puritan Bennett, Pleasanton, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/897,844

[22] Filed: Jul. 21, 1997

[51] Int. Cl.⁷ .......................................................... A61B 5/04
[52] U.S. Cl. .......................... 600/383; 600/393; 600/544; 600/546
[58] Field of Search ...................................... 607/152, 153, 607/139, 140, 141, 11; 600/372, 382–397, 544–546

[56] References Cited

U.S. PATENT DOCUMENTS

| | | |
|---|---|---|
| 796,533 | 8/1905 | Bayner . |
| 3,447,537 | 6/1969 | King . |
| 3,610,250 | 10/1971 | Sarbacher . |
| 4,365,634 | 12/1982 | Bare et al. . |
| 4,522,211 | 6/1985 | Bare et al. . |
| 4,537,198 | 8/1985 | Corbett . |
| 4,729,377 | 3/1988 | Granet et al. . |
| 4,736,752 | 4/1988 | Munck et al. . |
| 4,763,660 | 8/1988 | Kroll et al. . |
| 4,765,343 | 8/1988 | Brenman et al. . |
| 4,928,696 | 5/1990 | Henderson et al. ..................... 600/544 |
| 4,957,109 | 9/1990 | Groeger et al. . |
| 5,042,981 | 8/1991 | Gross . |
| 5,211,174 | 5/1993 | Imram . |
| 5,289,822 | 3/1994 | Highe et al. . |
| 5,295,482 | 3/1994 | Clare et al. . |
| 5,305,746 | 4/1994 | Fendrock . |
| 5,327,888 | 7/1994 | Imran . |

(List continued on next page.)

FOREIGN PATENT DOCUMENTS 2590800  6/1987  France .

OTHER PUBLICATIONS

The Hydro Dot, NeuroMonitoring System; Rochester Electro–Medical, Inc., Tampa, Florida.
Good Nights Sleep; Sedalia, Missouri, Sunday.
Check into sleep "hotel", Spring, 1997, p. 7.
'Aspects' of a knock out by Judy String, Staff Write, Mass High Tech, Mar. 24–30, 1997; vol. 15, Issue 12, p. 1+.

*Primary Examiner*—Linda C. M. Dvorak
*Assistant Examiner*—David M. Ruddy
*Attorney, Agent, or Firm*—Hovey, Williams Timmons & Collins

[57] ABSTRACT

A flexible, lightweight, inexpensive, and easy to attach sensor mask (10) for placement on a patient (11) for monitoring physiological signals of the patient is disclosed. The sensor mask includes an elongated flexible substrate (12); a plurality of electrodes (14) spaced along the length of the substrate and configured for placement against the patient for sensing the physiological signals; and at least one electrical connector (16) electrically coupled with the electrodes for delivering the physiological signals sensed by the electrodes to a recording/analyzing device. The electrodes are formed of patches of conductive ink that are deposited on the substrate at spaced locations along the length thereof. The electrical connector includes terminals formed of conductive ink deposited on the substrate and is electrically coupled with the electrodes by a plurality of lines of conductive ink deposited on the substrate.

11 Claims, 1 Drawing Sheet

U.S. PATENT DOCUMENTS

| | | |
|---|---|---|
| 5,331,959 | 7/1994 | Imran . |
| 5,337,748 | 8/1994 | McAdams et al. . |
| 5,341,806 | 8/1994 | Gadsby et al. .......................... 128/640 |
| 5,345,934 | 9/1994 | Highe et al. . |
| 5,352,315 | 10/1994 | Carrier et al. . |
| 5,353,793 | 10/1994 | Bornn . |
| 5,368,041 | 11/1994 | Shambroom . |
| 5,381,804 | 1/1995 | Shambroom . |
| 5,437,999 | 8/1995 | Diebold et al. . |
| 5,479,934 | 1/1996 | Imran . |
| 5,520,683 | 5/1996 | Subramaniam et al. . |
| 5,527,357 | 6/1996 | Springer, Jr. . |
| 5,540,722 | 7/1996 | Clare et al. . |
| 5,564,433 | 10/1996 | Thornton . |
| 5,567,037 | 10/1996 | Ferber . |
| 5,660,177 | 8/1997 | Faupel et al. ........................... 600/386 |
| 5,746,207 | 5/1998 | McLaughlin et al. .................. 128/639 |
| 5,772,591 | 6/1998 | Cram ....................... 600/383 |
| 5,813,404 | 9/1998 | Devlin et al. ........................... 600/544 |
| 5,865,741 | 2/1999 | Kelly et al. ............................ 600/386 |

SENSOR MASK AND METHOD OF MAKING SAME

BACKGROUND OF THE INVENTION

1. Field of the Invention

The present invention relates to a sensor mask for placement on a patient for monitoring physiological signals. More particularly, the present invention relates to such a sensor mask that is highly flexible, lightweight, and inexpensive and that can be quickly and easily attached to and removed from a patient.

2. Description of the Prior Art

Electrodes are commonly used for sensing and monitoring physiological signals such as eletroencephalographic (EEG) signals, electrooculargraphic (EOG) signals, or electromyographic (EMG) signals for diagnosing and treating certain medical conditions. For example, to diagnose and treat sleep disorders such as sleep apnea, a plurality of electrodes are placed on a patient's scalp and face to sense physiological signals representative of brain waves, eye movements, facial muscle movements, and respiration. The signals sensed by the electrodes are then recorded and analyzed to diagnose and treat the sleep disorder.

Unfortunately, existing electrodes are uncomfortable, difficult and time-consuming to attach, and costly, especially when more than one electrode is used at a time. This is because prior art electrodes are typically secured on a patient individually with tape and/or adhesives then each individually wired to a recording/analyzing device with a plurality of wires. This arrangement results in a tangle of wires that is uncomfortable and that interferes with the patient's natural movements, making it difficult for the patient to sleep. Moreover, the attachment and wiring of all the electrodes often takes over an hour to complete, thus inconveniencing both the patient and the medical personnel monitoring the patient and increasing the cost of a monitoring session.

Sensor devices having a plurality of individual pre-wired electrodes directly mounted on a mask that fits over a patient's head or face have been developed to alleviate some of the above-described problems. However, known sensor masks still utilize individual electrodes that are merely attached to a mask or electrodes formed from printed circuits of thick foil material and therefore are bulky, heavy and uncomfortable to wear. Moreover, known sensor masks are expensive to manufacture and therefore must be frequently sanitized and reused.

SUMMARY OF THE INVENTION

The present invention overcomes the limitations described above by providing a sensor that is flexible, lightweight, comfortable to wear and inexpensive and that can be quickly and easily attached to and removed from a patient. The sensor mask of the present invention broadly includes an elongated flexible substrate configured for placement on a patient; a plurality of electrodes mounted to and spaced along the length of the substrate and configured for placement against the patient for sensing the physiological signals; and at least one electrical connector electrically coupled with the electrodes for delivering the physiological signals sensed by the electrodes to a recording/analyzing device. Advantageously, the electrodes are formed from patches of conductive ink that are deposited on the substrate at spaced locations along the length thereof. Similarly, the electrical connector is electrically coupled with the electrodes by a plurality of lines of conductive ink deposited on the substrate between the electrical connector and the electrodes.

By forming the electrodes and electrical connector directly on the flexible substrate with conductive ink, the sensor mask of the present invention is highly flexible, lightweight, easy to attach and comfortable to wear. Moreover, since all of the electrodes are electrically coupled to a connector attached to the substrate, the sensor mask can be quickly and easily coupled with a recording/analyzing device by merely attaching a single cable between the recording/analyzing device and the connector. Thus, the sensor mask can be quickly and easily placed on a patient and used, thus reducing the time and costs associated with monitoring sessions.

Additionally, the entire sensor mask of the present invention can be quickly and easily manufactured at a minimum cost. The sensor mask can therefore be economically disposed of after a single use, eliminating the need to clean and sanitize the sensor mask.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENTS

Figure 1:
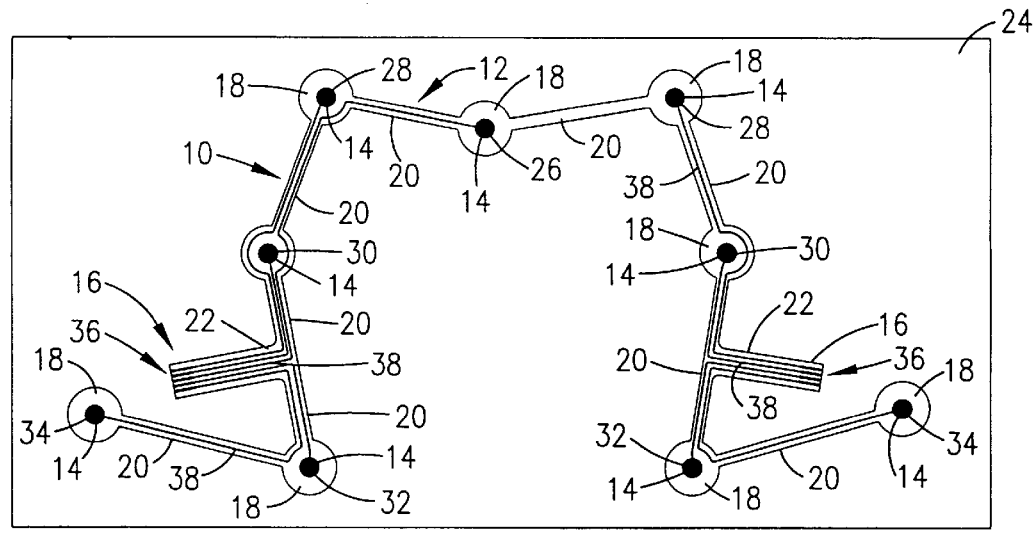
FIG. 1 is a plan view of a sensor mask constructed in accordance with a preferred embodiment of the present invention showing the sensor mask before it has been cut from its underlying sheet of substrate.

FIG. 1 illustrates a sensor mask 10 constructed in accordance with a preferred embodiment of the present invention. The sensor mask is configured for placement on the face or other region of a patient 11 for sensing physiological signals such as eletroencephalographic (EEG) signals, electrooculargraphic (EOG) signals, or electromyographic (EMG) signals. These sensed signals are then analyzed by a recording/analyzing device for diagnosing and treating certain medical conditions such as sleep apnea and other sleep disorders.

The sensor mask 10 broadly includes a flexible substrate 12, a plurality of electrodes 14 formed on the substrate, and a pair of electrical connectors 16 formed on the substrate and electrically coupled with the electrodes. The substrate 12 is preferably formed of a flexible, lightweight, electrically non-conductive polyester, mylar, or kapton material having a thickness of approximately 0.004–0.006 inches, with a preferred thickness of approximately 0.005 inches. One such material is made by ICI Films under the tradename of Melinex.

Figure 2:
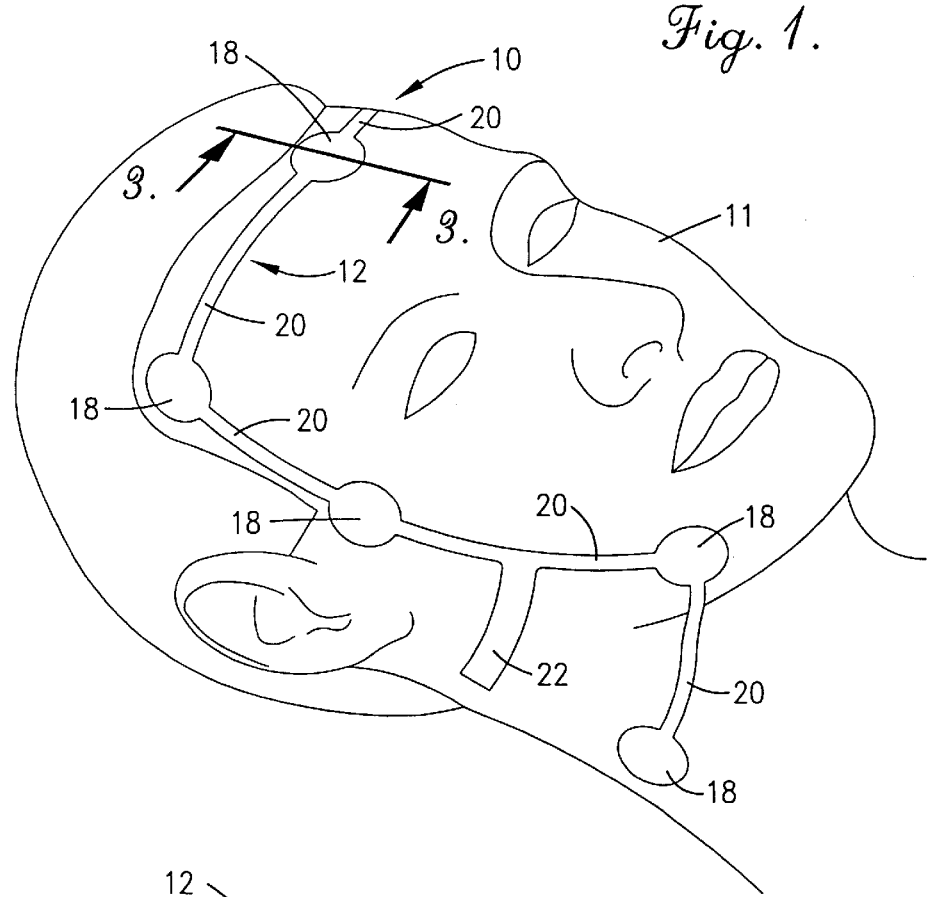
FIG. 2 is a perspective view of the sensor mask shown attached to a patient's face.

The substrate 12 is preferably formed in an elongated, thin, generally U-shaped strip having a pair of outwardly extending wings so that it is configured to lie flat over a patient's face and neck as illustrated in FIG. 2. The substrate may also be formed in other shapes and sizes for placement over other portions of the patient's body.

The illustrated substrate 12 includes nine spaced, enlarged, circular regions 18 connected by a plurality of interconnecting strips 20. The circular regions are each approximately ½–1½" in diameter, and preferably approximately 1" in diameter. The interconnecting strips are each approximately ¼–½" wide and range from 2–3" in length. The substrate also includes a pair of elongated, outwardly extending and slightly wider strips 22 for supporting the electrical connectors 16 as described below. As illustrated in FIG. 1 and as described in more detail below, the substrate 12 is preferably cut from a sheet 24 of substrate material to form an elongated mask or template in the shape illustrated in FIG. 2.

The electrodes 14 are formed of circular patches of conductive ink deposited on one face of the enlarged circular regions 18 of the substrate 12. Each electrode is approximately ¼–½" in diameter, and preferably approximately ⅜" in diameter. The conductive ink is preferably made of a silver chloride compound such as that sold by Poly-Flex Circuits or Creative Materials, but may also be made of other suitable conductive materials that can be deposited on a substrate. Once deposited on the substrate, the conductive ink adheres to the surface of the substrate and has a thickness of approximately 0.0005 inches. Since the substrate itself has a thickness of approximately 0.005 inches, the conductive ink comprises little of the overall thickness of the sensor mask and has an insignificant profile relative to the substrate. Thus, the conductive ink does not reduce the flexibility of the substrate. In contrast, prior art sensor masks include individual electrodes that are merely attached to a mask or electrodes formed from printed circuits of thick foil material that greatly reduce the flexibility of the sensor masks. Thus, the electrodes have a thickness no greater than 25% of the thickness of the substrate.

In preferred forms, the sensor mask 10 includes nine electrodes 14 strategically positioned along the length of the substrate 12 for sensing particular electrical signals representative of the condition and movement of the patient 11. Specifically, the sensor mask includes a centrally located ground electrode 26; a pair of opposed EEG electrodes 28 configured for placement on opposite sides of the patient's forehead for sensing electrical wave forms representative of the electrical activity of the patient's brain; a pair of opposed EOG electrodes 30 configured for placement on opposite sides of the patient's eyes for sensing electrical wave forms representative of the patient's eye movements; a pair of opposed EMG electrodes 32 configured for placement on opposite sides of the patient's mouth and chin for sensing electrical wave forms representative of the patient's mouth and chin movements; and a pair of reference electrodes 34 that sense reference signals that are used in connection with the EEG signals.

The electrical connectors 16 are formed on the outwardly extending strips 22 of the substrate 12 and are configured for attachment to the cables of a recording/analyzing device for delivering the signals sensed by the electrodes thereto. Each electrical connector preferably includes a plurality of spaced terminals 36 Chat are formed of short lines of conductive ink deposited on one face of the strips 22. The terminals are each electrically coupled with one of the electrodes 14 by lines of conductive ink 38 deposited on the interconnecting strips 20 of the substrate.

METHOD OF MANUFACTURE AND USE

The sensor mask 10 of the present invention is preferably manufactured by first depositing a plurality of spaced circular patches of conductive ink on one face of the sheet 24 of flexible substrate to form the spaced electrodes 14. Then, short sections of conductive ink are deposited on the substrate 12 to form the terminals 36 of the connectors 16. Lines of conductive ink are next deposited on the substrate between the terminals and the electrodes to electrically couple the terminals with the electrodes. The conductive ink that forms the electrodes, terminals, and interconnecting lines is preferably simultaneously silk screened on the sheet 24 of substrate with a silk-screening printer.

The substrate sheet 24 is then cut slightly outboard of the periphery of the electrodes 14, interconnecting lines 38 and connectors 16 to form the sensor mask 10 in the shape illustrated in FIG. 2. The waste portion of the substrate is then discarded or recycled.

Figure 3:
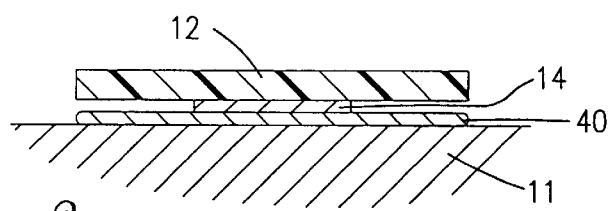
FIG. 3 is an enlarged section view taken along line 3—3 of FIG. 2 showing the layers of the mask and conductive gel when placed on a patient.

In use, the sensor mask 10 is placed over a patient's face and neck as illustrated in FIG. 2 so that the electrodes 14 are placed against the patient's skin. A thin layer of electro-gel 40 may be placed on the patient's skin directly under the electrodes as illustrated in FIG. 3 to improve the conductivity between the patient's skin 11 and the electrodes. The thickness of the layers shown in FIG. 3 are not to scale and are greatly exaggerated for clarity.

An insulative tape such as surgical tape manufactured by the 3M Corporation may be placed under the lines of conductive ink connecting the electrodes to the connectors 16 to insulate the patient 11 from all portions of the sensor mask except the electrodes. The connectors 16 are then coupled with the cables of a recording/analyzing device to deliver the electrical signals sensed by the electrodes to the recording/analyzing device. Once the diagnosis and/or treatment session has been completed, the sensor mask is merely removed from the patient and discarded or recycled.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by letters patent includes the following:

1. A sensor mask for placement on a patient for monitoring physiological signals of the patient, said sensor mask comprising:

an elongated flexible substrate;

a plurality of electrodes spaced along the length of the substrate and configured for placement against the patient for sensing the physiological signals, the electrodes each being formed of a patch of conductive ink deposited on said substrate, the electrodes including a centrally located ground electrode for positioning near a midpoint of the patient's forehead, a pair of opposed EEG electrodes for placement on opposite sides of the patient's forehead, a pair of opposed EOG electrodes for placement on opposite sides of the patient's eyes, a pair of opposed EMG electrodes for placement on opposite sides of the patient's mouth, and a pair of reference electrodes for placement on the patient's neck; and an electrical connector electrically coupled with said electrodes by a plurality of lines of conductive ink deposited on said substrate between said electrical connector and said electrodes for delivering the physiological signals sensed by said electrodes to a recording/analyzing device.

2. The sensor mask as set forth in claim 1, wherein said substrate presents a thickness of approximately 0.004–0.006 inches.

3. The sensor mask as set forth in claim 1, wherein said conductive ink deposited on said substrate presents a thickness of approximately 0.0005 inches.

4. The sensor mask as set forth in claim 1, said substrate being formed of polyester material.

5. The sensor mask as set forth in claim 1, said conductive ink being a silver chloride ink.

6. The sensor mask as set forth in claim 1, including nine electrodes.

7. The sensor mask as set forth in claim 1, said substrate being configured for placement over the patient's face.

8. A sensor mask for placement on a patient for monitoring physiological signals of the patient, said sensor mask comprising:

a flexible substrate including a plurality of spaced, enlarged regions interconnected by a plurality of relatively thin interconnecting strips;

a plurality of electrodes configured for placement against the patient for sensing the physiological signals, the electrodes including a centrally located ground electrode for positioning near a midpoint of the patient's forehead, a pair of opposed EEG electrodes for placement on opposite sides of the patient's forehead, a pair of opposed EOG electrodes for placement on opposite sides of the patient's eyes, a pair of opposed EMG electrodes for placement on opposite sides of the patient's mouth, and a pair of reference electrodes for placement on the patient's neck, the electrodes each comprising a patch of conductive ink deposited on one of said enlarged regions of said substrate;

a plurality of lines of conductive ink deposited on said interconnecting strips and connected with said electrodes; and an electrical connector electrically coupled with said lines of conductive ink for delivering the physiological signals sensed by said electrodes to a recording/analyzing device.

9. The sensor mask as set forth in claim 8, said enlarged regions being circular in shape.

10. The sensor mask as set forth in claim 9, said enlarged regions each having a diameter of approximately ¼"–½".

11. The sensor mask as set forth in claim 8, said interconnecting strips each being approximately ¼"–½" in width and approximately 2"–3" in length.

* * * * *